United States Patent [19]

Wedemeyer et al.

[11] 3,946,081

[45] Mar. 23, 1976

[54] OXIDATIVE SPLITTING OF UNSATURATED HYDROCARBONS

[75] Inventors: Karl-Friedrich Wedemeyer; Laszlo Imre, both of Cologne, Germany

[73] Assignee: Bayer Aktiengesellschaft, Leverkusen, Germany

[22] Filed: Dec. 27, 1972

[21] Appl. No.: 318,961

[30] Foreign Application Priority Data
Jan. 13, 1972 Germany............................ 2201411

[52] U.S. Cl...... 260/597 R; 260/586 R; 260/604 R; 260/606; 260/598; 260/590 R; 260/592
[51] Int. Cl.² .......................................... C07C 45/04
[58] Field of Search.... 260/604 R, 597, 606, 586 R, 260/598, 580 R

[56] References Cited
UNITED STATES PATENTS

| | | | |
|---|---|---|---|
| 2,990,427 | 6/1961 | Caldwell | 260/604 R |
| 3,600,443 | 8/1971 | Cevidelle | 260/604 R |

*Primary Examiner*—James O. Thomas, Jr.
*Assistant Examiner*—James H. Reamer
*Attorney, Agent, or Firm*—Burgess, Dinklage & Sprung

[57] ABSTRACT

In a process wherein a hydrocarbon containing a C-C-double bond is oxidatively split with both C atoms of the double bond being converted to carbonyl functions, the improvement which comprises contacting the hydrocarbon with an oxygen-containing gas at an elevated temperature in the presence of at least one oxide of an element of the V, VI or VII auxiliary group of the periodic system (Mendelejev) as catalyst. Preferred catalysts are vanadium, niobium, tantalum, chromium, molybdenum tungsten, uranium, manganese, technetium, or rhenium oxide in stages of oxidation ranging from the maximum to the free metal, preferably on a carrier. Preferred hydrocarbons are ethylene and cyclopentene. Carbonyl functions, e.g. aldehyde or acid, are formed at each carbon making up the double bond.

15 Claims, No Drawings

OXIDATIVE SPLITTING OF UNSATURATED HYDROCARBONS

The present invention relates to the splitting by oxidation of hydrocarbons which contain a carbon - carbon double bond. A known and generally applicable process for splitting C—C double bonds is the so-called ozone splitting process (Houben-Weyl: Methoden der Organischen Chemie, Stuttgart 1952, vol. 7/1, page 333). This process is often used to solve chemical problems in the laboratory but has not gained any technical importance since the production and handling of ozone is very complicated and considerable risks are run when dealing with the highly explosive ozonides which are obtained as intermediate products.

Apart from this generally applicable method there are a series of special methods which are specifically aimed at solving individual problems, for example, the splitting by oxidation of double bonds positioned adjacent aromatic rings using potassium permanganate (Houben-Weyl: Methoden der Organischen Chemie, Stuttgart 1952, vol. 7/1, page 345).

In addition chromic acid, nitric acid and osmium tetroxide as well as $H_2O_2$/osmium tetroxide have been used for splitting such activated double bonds (Houben-Weyl: Methoden der Organischen Chemie, Stuttgart 1952, vol. 7/1, page 347). Splitting by oxidation with lead tetraacetate or periodic acid is also known (Houben-Weyl: Methoden der Organischen Chemie, Stuttgart 1952, vol. 7/1 page 351). Oxidation of olefins in an inert atmosphere to form carbonyl compounds has also been described using chromium-VI-oxide as an oxidizing agent (L. M. Baker and W. L. Carrick, Journ. of Org. Chem. 33, 616 (1968). The $CrO_3$ is introduced in a stoichiometric ratio into the reaction and reduced to Cr (II).

All these methods are very complicated, require costly oxidizing agents and are dependent on special structural prerequisites.

For the splitting by oxidation of olefins on an industrial scale a series of catalytic processes are known from patent publications. In the German Patent Specification No. 722,707 the oxidation of ethylene and its homologs with oxygen-containing gases over activated carbon as the catalyst is described. For example the preparation of formaldehyde from ethylene is described. To control the reaction temperature the oxygen supply must be interrupted at regular intervals. Yields are not given in this patent specification. The formation of acetaldehyde and ethylene oxide as by-products is mentioned.

In the French Patent No. 1,349,902 the catalytic oxidation of low-molecular monoolefins with oxygen in the presence of oxides of the heavy metals copper, chromium, silver, tungsten, molybdenum and bismuth is described along with, for the purpose of activation, phosphoric acid and boric acid in a ratio of 1 : 5 to 5 : 1. Only the oxidation of propylene is dealt with in the examples. The oxidation which takes place is very unspecific and a large number of products form whose separation involves consideration outlay. In general acetic acid, acetaldehyde, formaldehyde, acetone, acetic ester and acrolein are produced together (cf., for example, Example 6 of that specification). In addition, a cnsiderable part of the propylene is broken down to carbon monoxide and carbon dioxide.

The catalytic oxidation of propylene is also described in the French Pat. No. 1,438,499. The essential difference between that patent and the French Patent No. 1,349,902 consists in that the phosphoric acid employed therein as an activator is replaced by arsenic acid and propylene-propane mixtures are used in the reaction. As an additional reaction product there is obtained propionaldehyde.

Molybdic acid-containing catalysts which contain activators such as Ce, V, Bi, Fe, Co, Mn, Ni, Ag, Ti, Zr, Cr or alkali or alkaline earth metals as well as borium and phospheric acid are given for the oxidation of propylene in the German Patent Specification No. 1,216,836. According to that process, more than half of the propylene is obtained in the form of acetone and a little acetaldehyde, from which it follows that the double bond of the propylene is only split to a small degree.

In the previously known technical processes for splitting olefins by oxidation, the heavy metal oxides are always used together with activators, such as phosphoric acid and/or arsenic acid and/or boric acid, these catalysts also having been employed in the form of the corresponding heteropolyacids or their salts.

It is accordingly an object of the invention to provide a process for the efficient oxidative splitting of doubly bonded hydrocarbons.

This is realized in accordance with the present invention pursuant to which the splitting by oxidation of hydrocarbons containing a carbon-carbon double bond using oxygen or oxygen-containing gases is effected with high selectivity with the formation of two compounds each containing a carbonyl function or one compound containing two carbonyl functions, if the hydrocarbons are reacted with oxygen or oxygen-containing gases, possibly in the presence of inert gases, at an elevated temperature in the presence of oxides of the elements of the V, VI, VII auxiliary group of the periodic system (Mendelejeff) as catalysts. Each of the carbon atoms constituting the double bond is converted to a carbonyl function.

The following elements may be mentioned for the metal oxides: vanadium, niobium, tantalum, chromium, molybdenum, tungsten, uranium, manganese, technetium and rhenium.

The intermediary oxides of these elements are preferably employed. By intermediary oxides in a metal-oxygen system there are to be understood all compounds of the metal with oxygen, in which the metal is not in its highest state of oxidation and not in the zero state of oxidation, but in an intervening state of oxidation (A. D. Wadsley, Nonstoichmetric Metal Oxides, Advances in Chemistry Series 39, Washington, D.C., 1963, S. 23 – 36). A. J. Hegedus inter alia in the Journal for Inorganic and General Chemistry, vol. 281 (1955), on the middle of page 65 gives for example as intermediary oxides of tungsten the following compounds in the state of oxidation between $WO_3$ and W:

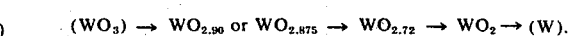

$(WO_3) \rightarrow WO_{2.90}$ or $WO_{2.875} \rightarrow WO_{2.72} \rightarrow WO_2 \rightarrow (W)$.

As catalysts according to the invention there may be mentioned oxides with the highest state of oxidation of the metal, such as $V_2O_5$, $Nb_2O_5$, $Ta_2O_5$, $CrO_3$, $MO_3$, $WO_3$, $UO_3$, $Mn_2O_7$, $Tc_2O_7$ and $Re_2O_7$ as well as all oxides between these with the highest state of oxidation and the metal of the state of zero oxidation, as so-called intermediary oxides.

As intermediary oxides there may be mentioned in particular:

$VO_{2.5-x}$, $x$ representing a number between 0 and 2.5, oxides of the homologous series $V_nO_{2n-1}$ (cf. S. Andersson and L. Jahnberg, Arkiv Kemi 21, 413 (1963)), $WO_{3-p}$, $p$ representing a number between 0 and 3, from 0 to 0.05 yellow, green, grey and black tungsten oxides with an $\beta$-$WO_3$ structure, $ReO_3$ type (cf. O. Glemser and H. Sauer, Journ. for Inorganic Chemistry, vol. 252 (1943), page 144, in particular page 158, as well as P. Gadó and L. Imre, Acta Chim. hung. 46, 166 (1965)), $W_{40}O_{118}$ (Shear-Structure, cf. P. Gadó and L. Imre, Acta Chim. hung. 46, 167 (1965)), compounds of the homologous series of the general formula $W_mO_{3m-2}$, e.g. $W_{20}O_{58}$ (cf. A. Magnéli, Acta Cryst. 6, 495, (1953)), also $W_{18}O_{49}$ (violet tungsten oxide, identical to $WO_{2.72}$, cf. citation A. J. Hegedus inter alia, page 65), $WO_{2.03}$-$WO_{2.00}$ (cf. lit. ref. O. Glemser and H. Sauer, page 158 at the bottom), as well as $W_3O$ (identical to $WO_{0.33}$ (G. Haegg and N. Schonberg, Acta Cryst. (Copenhagen) 7. 351 (1954); $MoO_{3-q}$, $q$ representing a number between 0 and 3, in particular $Mo_9O_{26}$, $Mo_8O_{23}$, $Mo_4O_{11}$, $MoO_2$ (cf. O. Glemser and G. Lutz, Journ. for Inorganic and General Chemistry, vol. 263 (1950), page 2, in particular pages 13 and 14) as well as other intermediary oxides from the homologous series of the sumation formula $Mo_mO_{3m-1}$ (cf. A. Magneli, Acta Cryst. 6, (1953)); other preferred intermediary molybdenum oxides are $MoO_{2.90}$, $MoO_{2.83}$, $MoO_{2.80}$ and $MoO_{2.75}$ (L. Kihlborg, Acta chem. scand. 13, 954 (1959)); as intermediary oxides of uranium there may be mentioned compounds of the formula $UO_{3-p}$, $p$ representing a number between 0 and 3, such as $UO_{1.75}$, $UO_2$, $UO_{2.50}$, $U_2O_5$, $U_3O_8$, $U_4O_7$, $U_{16}O_{37}$ and $U_{16}O_{38}$ (H. Remy, Manual of Inorganic Chemistry, 11th Edition, vol. II, Leipzig (1961), page 238 – 239); as intermediary oxides of rhenium there may be used those corresponding to to the formula $ReO_{3.5-y}$, $y$ standing for a number between 0 and 3.5.

Such intermediary oxides are obtainable for example by reduction of the oxide containing the metal in the highest state of oxidation with conventional reduction agents, such as hydrogen or ethylene, by reaction of the metal oxide of the highest state of oxidation with the metal, or by thermal decomposition of the metal oxides containing the metal in the highest state of oxidation (cf. the above cited literature). With the aid of these conversion methods it is of course possible to manufacture oxides with a lower state of oxidation of the metal from intermediary oxides with a higher state of oxidation (cf. inter alia J. Neugebauer, L. Imre and T. Millner in solid-state Physics, Akademie-Verlag Berlin 1961, page 227 onwards).

The intermediary oxides can also be manufactured from suitable starting compounds under the reaction conditions. For example, $WO_3$ can be reduced with ethylene at temperature above about 200°C to form intermediary oxides.

The catalysts are preferably on carriers. As catalyst carriers there may be mentioned for example: silicic acid, natural or synthetic silicates, aluminum oxide, spinel, pumice stone and titanium dioxide. The respective metal of the metal oxides to be used according to the invention can be employed as the carrier. The catalyst can be used in the form of pills, rolls or pellets, for example, in the form of pellets of 0.5 – 6 mm diameter. The carrier catalyst can be manufactured in general by impregnating the carrier with the solution of a suitable metal salt, drying it and converting the metal compound in a manner known per se, e.g. by thermal decomposition, into the oxide. For example to produce a molybdenum oxide carrier catalyst an aqueous solution of ammonium molybdate is applied to the carrier material by soaking and then converted by thermal treatment into molybdenum oxide. The metal oxides according to the invention can be used in their pure form; however, mixtures of the different metal oxides can be used on one carrier.

The metal oxide content in the catalyst can be varied within wide limits. It can amount to 100 % for example if work is performed without the carrier. If a carrier is used, the amount of metal oxides in the catalyst can lie between about 0.01 and 50 % by weight. Concentrations of about 0.1 – 10 % by weight metal oxide are preferably used in the catalyst.

The temperature range of the splitting reaction can be varied within wide limits. In general work is carried out at temperatures from about 150°– 650° C, preferably about 250°– 450° C. The catalytic splitting of the hydrocarbon compound can be performed at normal pressure, elevated or reduced pressure and in the gas phase, in the liquid phase or in the mixed phase. Work can be carried out in the presence of inert compounds, e.g. inert gases such as nitrogen, carbon dioxide or vapour. The process of the invention is preferably carried out in the gas phase. The catalysts may be in a fixed bed, e.g. fixedly arranged in one or more reaction tubes, to ensure improved transfer of heat but they may also be in a fluidized bed or in another kind or agitated catalyst bed. When working in the gas phase in the presence or in the absence of inert gases such conditions are to be observed regarding initial concentrations, temperature and pressure so that the hydrocarbons are in the gas phase upon entry into the reactor. Within the range for working in the gas phase, pressure, temperature, gas composition and flow velocity can be varied within wide limits.

The amount of oxygen or oxygen-containing gases, which is used according to the process of the invention for the splitting of unsaturated hydrocarbons, can be varied within wide limits. For example, per mole of unsaturated hydrocarbon there may be used 0.005 – 200 moles of oxygen, calculated as pure oxygen. Within this range it is of course necessary to take into consideration the explosion limits applicable to the hydrocarbon used in admixture with oxygen 0.02 – 50 moles of oxygen are preferably used per mole of hydrocarbon.

An oxygen content of 0.04 – 10 moles per mole of unsaturated hydrocarbon is especially preferred. The oxygen can of course be used in admixture with inert gases. An inert gas is most expediently added, for example, when the hydrocarbon/oxygen mixtures arising within the given ranges come near to the explosion limits. The addition of an inert gas may also be expedient when the flow velocity is to be increased or the resulting reaction heat to be led off. For example, oxygen/nitrogen or oxygen/$CO_2$ mixtures can be employed with a contant of up to 98 % by volume, preferably up to 95 % by volume, of inert gas. When dilute oxygen is to be used with an inert gas, the use of air is especially preferred.

If the hydrocarbon is only partially reacted in the straight passage, the resulting splitting product and/or non-reacted starting product can be separated from the reaction product, possibly after cooling or partial or complete condensation of the gaseous reaction product by means of generally known methods, e.g. by fractionated distillation and said product recycled to the reaction. To achieve a high selectivity it may be expedient to carry out a partial reaction only. In this way almost complete catalytic splitting of the hydrocarbon compound takes place to produce the desired end product.

As hydrocarbons with a C — C double bond for use in the process of the invention there may be mentioned, for example, compounds of the general formula.

In the formula (I) $R_1$, $R_2$, $R_3$ and $R_4$ represent independently of each other hydrogen, an aryl group optionally substituted by at least one lower alkyl radical, a straight-chain or branched alkyl radical with up to 18 C atoms, optionally phenyl substituted when lower alkyl, or the radicals $R_1$ and $R_2$ together, or $R_3$ and $R_4$ together, contain not more than 20 C atoms and each, independently of each other, form a carbocyclic ring or the radicals $R_1$ and $R_3$ together with the C atoms of the C—C double bond are a carbocyclic ring with up to 24 C atoms and $R_2$ and $R_4$ each independently is hydrogen or a lower alkyl radical, e.g. $C_1$ -4 alkyl.

As straight-chain or branched alkyl radicals with up to 18 C atoms there may be mentioned for example: methyl, ethyl, propyl, n-butyl, isobutyl, tert.-butyl, pentyl, hexyl, heptyl, octyl, nonyl decyl, undecyl, dodecyl, pentadecyl, hexadecyl, octadecyl as well as their isomers. As phenyl groups which are substituted by a lower alkyl radical there may be mentioned: tolyl, ethylphenyl, propylphenyl, n-butylphenyl, tert.-butylphenyl. As lower alkyl radicals which are substituted by a phenyl radical there may be mentioned for example: phenylmethyl, phenylethyl, phenylpropyl, phenyl-tert.-butyl. As aryl radicals which can be substituted by lower alkyl there may be mentioned phenyl, diphenyl, naphtyl, anthracyl and phenanthryl radicals.

Examples of compounds of the general formula (I) to be used for the process according to the invention are preferably compounds wherein $R_1$, $R_2$ and $R_3$ each independently is hydrogen, a phenyl radical or a straight-chain or branched lower alkyl radical and $R_4$ is hydrogen or a straight-chain or branched alkyl radical with up to 18 C atoms, one of the alkyl radicals $R_1$, $R_2$, $R_3$ and $R_4$ being substituted by a phenyl group optionally substituted by at least one lower alkyl radical.

According to the process of the invention 1 molecule of a compound of the formula (I) is converted to 2 molecules of aldehyde or to 2 molecules of ketone or to 1 molecule of aldehyde and 1 molecule of ketone. For example, on reacting ethylene according to the process of the invention formaldehyde is produced on employing propylene an equimolecular mixture of acetaldehyde and formaldehyde is produced, on using isobutylene as the starting material there is produced acetone and formaldehyde, on using α-methylstyrene there is produced acetophenone and formaldehyde.

A further preferred group of compounds of the general formula (I) corresponds to the formula

wherein $w$ stands for a whole integer from 3 to 22, preferably 3 to 10.

A compound of the general formula (II) is converted to a dialdehyde according to the process of the invention. For example, glutardialdehyde is produced from cyclopentene and octanedial from cyclooctene in the process of the invention.

As compounds of the general formula (I) there can also preferably be used compounds of the formula

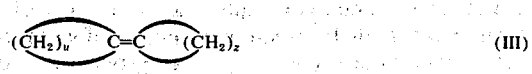

wherein $u$ and $z$ represent independently of each other a whole integer from 4 to 11, preferably 5 to 7.

According to the process of the invention, cyclic ketones are produced from compounds of the formula (III), e.g. 1,1'-dicyclopentylidene is converted to cyclopentanone.

As compounds of the general formulas (I) to (III) there may be mentioned the following unsaturated compounds.

ethylene, propylene, butene-(1), butene-(2), 2-methyl-propene, pentene-(1), pentene-(2), 2-methyl-butene-(1), 2-methyl-butene-(2), 2-methyl-butene-(3), hexene-(1), hexene-(2), hexene-(3), 2-methyl-pentene-(1), 2-methyl-pentene-(2), 2-methyl-pentene-(3), 2-methyl-pentene-(4), 3-methyl-pentene-(1), 3-methyl-pentene-(2), 2-ethyl-butene-(1), 2,2-dimethyl-butene-(3), 2,3-dimethyl-butene-(1), 2,3-dimethyl-butene-(2), heptene-(1), heptene-(2), heptene-(3), 2-methyl-hexene-(1), 2-methyl-hexene-(2), 2-methyl-hexene-(3), 2-methyl-hexene-(4), 2-methyl-hexene-(5), 3-methyl-hexene-(1) 3-methyl-hexene-(2), 3-methyl-hexene-(3), 3-methyl-hexene-(4), 3-methyl-hexene-(5), 2-ethyl-pentene-(1), 3-ethyl-pentene-(1), 3-ethyl-pentene-(2), 2,2-dimethyl-pentene-(3), 2,2dimethyl-pentene-(4), 2,3-dimethyl-pentene-(1), 2,3-dimethyl-pentene-(2), 2,3-dimethyl-pentene-(3), 2,3-dimethyl-pentene-(4), 2-methyl-3 -ethyl-butene-(3), 2,4-dimethyl-pentene-(1), 2,4-diemthyl-pentene-(2), 3,3-dimethyl-pentene-(1), 2,2,3-trimethyl-butene-(3), octene-(1), octene-(2), octene-(3), octene-(4), 2-methyl-heptene-(1), 2-methyl-heptene-(2), 2-methyl-heptene-(3), 2-methyl-heptene-(4), 2-methyl-heptene-(5), 2-methyl-heptene-(6), 3-methyl-heptene-(1), 3-methyl-heptene-(2), 3-methyl-heptene-(3), 3-methyl-heptene-(6), 2-ethyl-hexene-(1), 4-methyl-heptene-(1), 4-methyl-heptene-(2), 4-methyl-heptene-(3), 3-ethyl-hexene-(2), 3-ethyl-hexene-(3), 3-ethyl-hexene-(4), 3-ethyl-hexene-(5), 2,2-dimethyl-hexene-(3), 2,3-dimethyl-hexene-(1), 2,3-dimethyl-hexene-(2), 2,3-dimethyl-hexene-(3), 2,3-dimethyl-hexene-(4), 2,4-dimethyl-hexene-(2), 2,4-dimethyl-hexene-(4), 2,4-dimethyl-hexene-(5), 2,5-dimethyl-hexene-(1), 2,5-dimethyl-hexene-(2), 2,5-dimethyl-hexene-(3), 3,3-dimethyl-hexene-(1), 3,3-dimethyl-hexene-(4), 3,3-dimethyl-hexene-(5), 3,4- dimethyl-hexene(2), 2-methyl-3-ethyl-pentene-(2), 3-methyl-3-ethyl-pentene-(1), 2,2,3-trimethyl-pentene-(3), 2,2,3-trimethyl-pentene-(4), 2,2-dimethyl-3-ethyl-butene-(3), 2,2,4-trimethyl-pentene-(3), 2,2,4-trimethyl-pentene-(4), 2,3,3-trimethyl-pentene-(1), 2,3,3-trimethyl-pentene-(4), 2,3,4-trimethyl-pentene-(1), 2,3,4-trimethyl-pentene-(2), 2-methyl-3-isopropyl-butene-(3), heptadecene-(1), heptadecene-(8), octadecene-(1), octadecene-(9), 2-methyl-heptadecene-(2), 9-methyl-heptadecene-(8), 2,2-dimethylhexadecene-(3), 7,10-dimethyl-hexadecene-(8), 8-propyl-pentadecene-(7), nonadecene-(1), 2,6,10,14-tetramethyl-pentadecene-(1), 7-hexyl-tridecene-(6), eicosene-(1), eicosene-(9), 2-methyl-nonadecene-(2), 1-octyl-1-decyl-ethylene, 3-ethyl-octadecene-(2), 5,7,9-trimethyl-heptadecene-(4), 5-butyl-hexadecene-(4), 2,6,10,14-tetramethyl-hexadecene-(14), 2,6,10,14-tetramethyl-hexadecene-(15), 2,6,10,14-tetramethyl-7-methylene-pentadecane, docosene-(9), 8,11-dimethyl-eicosene-(10), 4-propyl-nonadecene-(3), tricosene-(11), 5-butyl-eicosene-(4), 9-octyl-heptadecene-(8), 10-nonyl-nonadecene-(9), cyclopentene, cyclohexene, 1-methyl-cyclopentene-(1), 1-methyl-cyclopentene-(2), 1-methyl-cyclopentene-(3), methylene-cyclopentane, cycloheptene, 1-methyl-cyclohexene-(1), 1-methyl-cyclohexene-(2), 1-methyl-cyclohexene-(3), methylene-cyclohexane, 1-ethyl-cyclopentene-(1), 1-ethyl-cyclopentene-(2), vinyl-cyclopentane, 1,1-dimethyl-cyclopentene-(2), 1,2-dimethyl-cyclopentene-(1), 1,2-dimethyl-cyclopentene-(2), 1,2-dimethyl-cyclopentene-(3), 3-methyl-1-methylene-cyclopentane, cyclooctene, 1-methyl-cycloheptene-(1), 1-methyl-cycloheptene-(4), 1-ethyl-cyclohexene-(1), 1-ethyl-cyclohexene-(2), ethylidene-cyclohexane, vinyl-cyclohexane, 1,1-dimethyl-cyclohexene-(2), 1,1-dimethyl-cyclohexene-(3), 1,2-dimethyl-cyclohexene-(1), 1,2-dimethyl-cyclohexene-(2), 1,3-dimethyl-cyclohexene-(1), 1,3-dimethyl-cyclohexene-(3), 1,3-dimethyl-cyclohexene-(4), 3-methyl-1-methylene-cyclohexane, 1,4-dimethyl-cyclohexene-(1), 1,4-dimethyl-cyclohexene-(2), 4-methyl-1methylene-cyclohexane, 1-propyl-cyclopentene-(1), 1-propyl-cyclopentene-(2), allyl-cyclopentane, 1-isopropyl-cyclopentene-(1), 1-isopropyl-cyclopentene-(2), isopropylidene-cyclopentane, 1-methyl-2-ethyl-cyclopentene-(1), 1-methyl-2-ethylidene-cyclopentane, 1,1,2-trimethyl-cyclopentene-(2), 1,2,3-trimethyl-cyclopentene-(1), 1,2,3-trimethyl-cyclopentene-(3), 1-methyl-cyclooctene-(1), 1-ethyl-cycloheptene-(1), 1-propyl-cyclohexene-(1), 1-propyl-cyclohexene-(2), 1-propyl-cyclohexen-(3), allyl-cyclohexane, 1-isopropyl-cyclohexene-(1),1-isopropyl-cyclohexene-(2), isopropylidene-cyclohexane, 1-methyl-2-ethyl-cyclohexene-(1), 1-methyl-3-ethyl-cyclohexene-(2), 1-methyl-3-ethyl-cyclohexene-(3), 1-methyl-'-ethylidene-cyclohexane, 1-methyl-3-vinyl-cyclohexane, 1-methyl-4-ethyl-cyclohexene-(3), 1,1,2-trimethyl-cyclohexene-(2), 1,1,3-trimethyl-cyclohexene-(4), 1,2,3-trimethyl-cyclohexene-(3), 1,2,4-trimethyl-cyclohexene-(1), 1,3,5-trimethyl-cyclohexene-(1), 1-butyl-cyclopentene-(1), 1-butyl-cyclopentene-(2), buten-(2)-yl-cyclopentane, buten-(3)-yl-cyclopentane, 1-sec.-butyl-cyclopenten-(2), 2-cyclopentyl-butene-(3), 1-isobutyl-cyclopentene-(2), 1-tert.-butyl-cyclopentene-(2), 1-methyl-2-propyl-cyclopentene-(1), 1-methyl-2-isopropenyl-cyclopentane, 1-methyl-3-isopropyl-cyclopentene-(1), 1,2-diethyl-cyclopentene-(1), cyclohexadecene, 1-methyl-cyclopentadecene-(1), 2-methyl-3-cyclohexyl-nonene-(2), 1-undecyl-cyclopentene-(2), cycloheptadecene, 1-dodecyl-cyclopentene-(2), 1-methyl-cycloheptadecene-(1), 1-tridecyl-cyclopentene-(2), 2,2,6,6-tetrapropyl-1-methylene-cyclohexane, 1-tetradecyl-cyclopentene-(2), 4-methyl-2,2,6,6-tetrapropyl-1-methylene-cyclohexane, 1-hexadecyl-cyclopentene-( 2), 1-octadecyl-cyclopentene-(2), bicyclo[2.2.1]heptene-(2), 2-methyl-bicyclo[2.2.1]heptene-(5), bicyclo[2.2.2]octene-(2), hexahydroindane, 2,2-dimethyl-bicyclo[2.2.1]heptene-(5), 1-cyclopentyl-cyclopentene-(2), bicyclo[5.3.0]decene-(2), $\Delta^1$-octaline, $\Delta^2$-octaline, 3a-methyl-3a,4,5,6,7,7a-hexahydro-indene, 2-methylene-hexahydroindane, 3,7-dimethyl-bicyclo[3.3.0]octene-(2), 2-propyl-bicyclo[2.2.1]heptene-(5), 1,2,3-trimethyl-bicyclo[2.2.1]heptene-(2), 1,7,7-trimethyl-bicyclo[2.2.1]heptene-(2), 3,3-dimethyl-2-methylene-bicyclo [2.2.1] heptane, 1-cyclohexyl-cyclopentene-(2), 3-methyl-bicyclo [5.3.0] decene-(3), 1-methyl-$\Delta^1$-octaline, 2-methylene-decaline, 2,2-dimethyl-3-ethylidene-bicyclo [2.2.1] heptane, 1,2,3,4-tetramethyl-bicyclo[2.2.1] heptene-(2), cyclohexylidene-cyclohexane, 1-ethyl-3-[cyclopenten-(2)-yl] -cyclopentane, 2-[buten -(3)-yl] -decaline, 1-ethyl-2-propyl-$\Delta^1$ -octaline, tricyclo[ 5.2.1.0$^{2.6}$]decene-(8), tricyclo[5.2.1.0$^{2.6}$]decene-(4), 1,2,3,4,4a,5,6,8a-octahydro-1,4-ethano-naphthaline, dicyclohexyl-cyclohexylidene-methane, 1,5-dicyclohexyl-3-[2-cyclohexyl-ethyl]-pentene-(2), styrene, propenyl-benzene, allylbenzene, isopropenyl-benzene, 1-methyl-2vinyl-benzene, 1-methyl-3-vinyl-benzene, 1-methyl-4-vinyl-benzene, buten-(1)-yl-benzene, buten-(2)-yl-benzene, buten-(3)-yl-benzene, (1-methyl-propenyl)-benzene, (1methyl-allyl)-benzene, (1-ethyl-vinyl)-benzene, (2-methyl-propenyl)-benzene, (2-methyl-allyl)-benzene, 1-methyl-2-propenyl-benzene, 1-methyl-2-allyl-benzene, 1-methyl-3-propenyl-benzene, 1-methyl-3-allyl-benzene, 1-methyl-4-propenyl-benzene, 1-methyl-4-allyl-benzene, 1-methyl-2-isopropenyl-benzene, 1-methyl-3-isopropenyl-benzene, 1-methyl-4-isopropenyl-benzene, 2-ethyl-1-vinyl-benzene, 3-ethyl-1-vinyl-benzene, 4-ethyl-1-vinyl-benzene, 1,2-dimethyl-3--vinyl-benzene, 1,3-dimethyl-2-vinyl-benzene, 1,2-dimethyl-4-vinyl-benzene, 1,4-dimethyl-2-vinyl-benzene, 1,3-dimethyl-4-vinyl-benzene, 1,3-dimethyl-5-vinyl-benzene, penten- (1)-yl-benzene, penten-(2)-yl-benzene, penten-(3)-yl-benzene, penten-(4)-yl-benzene, [1-methyl- buten-(1)-yl]-benzene, [1-methyl- buten-(3)-yl]-benzene, [2-methyl- buten-(1)-yl]benzene, [3-methyl-buten-(1)-yl]-benzene, [3-methyl-buten-(2)-yl]-benzene, [1-ethyl-propenyl]-benzene, [1-ethyl-allyl]-benzene, [1,2-dimethyl-propenyl]-benzene, 1-methyl-4-[buten-(2)-yl]-benzene, 1-methyl-2-[1-methyl-propenyl]-benzene, 1-methyl-3-[1-methyl-propenyl]-benzene, 1-methyl-4-[1-ethyl-vinyl]-benzene, 1-methyl-4-[2-methyl-propenyl]-benzene, 1-methyl-4-[2-methyl-allyl]-benzene, 1-ethyl-3allyl-benzene, 1-ethyl-4-allyl-benzene, 4-isopropyl-1-vinyl-benzene, 1,4-dimethyl-2-propenyl-benzene, 1,3-dimethyl-4-propenyl-benzene, 1,2-dimethyl-3-isopropenyl-benzene, 1,2-dimethyl-4-isopropenyl-benzene, 1,3-dimethyl-4-isopropenyl-benzene, 1,3,5-trimethyl-2-vinyl-benzene, 1,2,4-trimethyl-5-vinyl-benzene, hexen-(5)-yl-benzene, decen-( 1)-yl-benzene, 4-(2-ethyl-hexyl)-1-vinyl-benzene, 1,3-dimethyl-4-[2-propyl-penten(1)-yl]-benzene, undecen-(1)-yl-benzene, dodecen-(1)-yl-benzene, [1-methyl-undecen-(1)-yl]-benzene, (1-decyl-vinyl)-benzene, 1,3-dimethyl-4-[2-butyl-hexen-(1)-yl]-benzene, 1,2-bis-[3,3-dimethyl-bicyclo[2.2.1]heptyl-(2)]-ethylene, indene, 1,2-dihydro-naphthaline, 1-methyl-indene, 2-methyl-indene, 3-methyl-indene, cyclopenten-(2)-yl-benzene, 6,7-dihydro-5H-benzocycloheptene, 1-methyl-5,8-dihydro-naphthaline, 2-vinyl-5,6,7,8-tetrahydro-naphthaline, 1,2-dimethyl-3,4-dihydro-naphthaline, benzylidine-cycloheptane, 2-cyclohexyl-1-phenyl-ethylene, 1-[buten-(2)-yl]-tetraline, 1-vinyl-naphthaline, 1-propenyl-naphthaline, 1-allyl-naphthaline, 1-isopropenyl-naphthaline, 1-[1-methyl-buten-(1)-yl]-naphthaline, 1,2-diphenyl-ethylene, 1,1-diphenyl-ethylene, 2-vinyl-biphenyl, 3-vinyl-biphenyl, 4-vinyl-biphenyl, 1,3-diphenyl-propene, 1,2-diphenyl-propene-(1), 1-phenyl-2-o-tolyl-ethylene, 1,1-diphenyl-propene-(1), 2-isopropenyl-biphenyl, 1,4-diphenyl-butene-(1), 1,4-diphenyl-butene-(2), 1,3-diphenyl-butene-(2), 1,3-diphenyl-butene(1), 1,3-diphenyl-butene-(3), 2-methyl-1,3-diphenyl-propene, 1,2-diphenyl-butene-(1), 2,3-diphenyl-butene-(2), 2,3-diphenyl-butene-(1), 1,2-di-p-tolyl-ethylene, 1,1-diphenyl-butene-(1), 2-[buten-(1)-yl]-bi phenyl, 1-[2-methyl-cyclopenten-(1)-yl]-naphthaline, 1-ethyl-3,4-dihydro-phenanthrene,2-methyl-1,4-diphenyl-butene-(1), 1,2-diphenyl-pentene-(3), 3,4-diphenyl-hexene-(3), 2-ethyl-1,1-diphenyl-butene-(1), 2-[hexen-(1)-yl]-biphenyl, 1,2-bis-(2,4,6-trimethyl-phenyl)-ethylene, 1,1-diphenyl-nonene-(1), 5,6-diphenyl-decene-(5), 1,1-dibenzyl-hexadecene-(1), 1,2-bis-(2,4,6-triisopropyl-phenyl)-ethylene,9-isopropylidene-fluorene, 1-cyclopentyl-1,2-diphenyl-ethylene, 1-isobutyl-2-phenyl-3,4-dihydro-naphthaline, 2,2-dimethyl-3-[naphthyl-(1)-methylene]bicyclo [2.2.1]heptane, 2-vinyl-phenanthrene, 2-isopropenyl-anthracene, 9-propenyl-phenanthrene, 9-allyl-phenanthrene, 1,2-dicyclohexyl-1,2-diphenyl-ethylene, 1-phenyl-2-[naphthyl-(1)]-ethylene, 1-phenyl-1-[naphthyl-(1)]-ethylene, 2-phenyl-3-[naphthyl-(1)]-butene-(2), triphenyl-ethylene, 1-phenyl-2-[biphenylyl-(4)]-ethylene, phenyl-[fluoroenylidene-(9)]-methane, cyclohexyl-triphenyl-ethylene, 1,2-di-[naphthyl-(1)]-ethylene, 1,1-di-[naphthyl-(1)]-ethylene, 1,2-bis-[4-methyl-naphthyl-(1)]-ethylene, tetraphenylethylene and the like.

In general the process according to the invention is carried out as follows:

The unsaturated hydrocarbon to be split is mixed in gaseous or vaporous form with oxygen or an oxygen/inert gas mixture, e.g. air, for example in a well fluidized mixing chamber or by means of a mixing nozzle. The resulting starting mixture is heated to the reaction temperature, for example by treatment in a preheater and then contacted with the catalyst, e.g. introduced into a fluidized bed or conducted over the contact material fixedly arranged in a bundle of tubes. If a tubular reactor is employed, the reaction tubes can be surrounded by a heat transmission agent, e.g. by a salt melt, for controlling the temperature. The fluidized bed can also be provided with builtin devices for controlling the temperature. The reaction mixture leaving the reactor is passed on for processing. It can, for example, be condensed or subjected to washing. During washing the desired products are in general isolated and separated from any non-reacted olefins. In the case of splitting by oxidation of ethylene to form formaldehyde, the washing for example is expediently carried out with water. In this way a commercially available aqueous formaldehyde solution is obtained and the residual gas can be readjusted to the initial concentration by admixture of the consumed parts of ethylene and/or oxygen. In this way a continuous cycle is obtained. When following this procedure it is expedient to use a multistage washer.

The heating of the unsaturated hydrocarbon and oxygen or of the oxygen-containing gas to the reaction temperature can also be carried out separately. For example, both reactants can be separately introduced into a fluidized bed. In so doing it may be expedient to introduce the unsaturated hydrocarbon at a point in the reaction space which lies a little in front of the point at which oxygen is introduced. If the reaction is carried out in the presence of inert gases or vapors, then steam for example can also be used as an inert gas. For example, the water vapor can be heated to the desired reaction temperature and oxygen, optionally as air, metered into said vapor. Thereafter the unsaturated hydrocarbon can be added in vaporous, gaseous or in liquid form and this mixture conducted over the catalyst. The working up of the mixture leaving the reactor is then expediently performed in a washer; it can however be carried out by indirect cooling, possibly by fractionated cooling.

When using air as an oxygen-containing gas it may prove necessary, if the reaction is only partial, to separate the nonreacted unsaturated hydrocarbon from the nitrogen. This separation can be carried out by pressure distillation or by washing, e.g. with diesel oil with subsequent final heating of the nonreacted hydrocarbon. It is particulary economical to blow the hydrocarbon out of the diesel oil with the air required for the repeat reaction at an elevated temperature. Depending on the concentration ratios (partition coefficients) it may be sufficient to conduct a side stream of the recycled gas to the working up step.

The invention will be further described in the following illustrative examples wherein all parts are by weight unless otherwise expressed.

EXAMPLE 1

10 g of molybdenum oxide of the formula $Mo_9O_{26}$ as a catalyst on 2.5 g of quartz wool with a volume of about 25 cm³ are introduced into an electrically heated reaction tube 70 cm in length and 1.8 cm in diameter. The catalyst is prepared as follows: a 5 % $(NH_4)_2 MoO_4$ solution, which corresponds to a content of 10 g $MoO_3$, is evaporated with 2.5 g of quartz wool on a water bath and subsequently converted by thermal decomposition to $MoO_3$ by heating to 600° C in air. The resulting $MoO_3$ is then reduced at 480°C in a 1.5 % water-containing hydrogen atmosphere to form $Mo_9O_{26}$.

25.6 l of ethylene and 1 l of oxygen in the gas phase are conducted hourly at 440° C over the catalyst after passing through a Raschig ring-filled mixing chamber having a volume of 500 cm³. This correponds to a starting gas composition of 3.76 % by volume of oxygen and 96.24 % by volume of ethylene. The resulting formaldehyde in the reaction gas is identified with the aid of gas chromatography, infra-red spectroscopy and mass spectroscopy. The quantitative analysis of the reaction product was carried out both by gas chromatography and titration. For the gas chromatographic determination of the concentration of formaldehyde and water formed as a by-product a Porapak-N column was used and a Porapak-S column for determining the conversion rate of oxygen. The titrimetric determination of the formaldehyde was carried out according to the sulfite method (cf. J. F. Walker, Formaldehyde, Reinhold Publishing Corporation, New York, 1964, page 562). For this purpose the gas stream is conducted through 3 gas flasks each containing 100 cm³ of water and the aqueous solution analyzed. The conversion amounted to 15.8 % based on the amount of oxygen used. After a reaction period of 48 hours 15.9 g of formaldehyde are found which corresponds to a selectivity of 84 %. In the case of large-scale reactions it is possible to isolate the largest part of the formaldehyde in the form of polyoxymethylene from the gas stream in compact form in suitable separation vessels. Polyoxymethylene obtained in this way had a water content of less than 20 % by weight. Thus polymerization and recovery in the form of polyoxymethylene is just as suitable for isolating the formaldehyde as washing out with water, aqueous formaldehyde solutions being obtained which are in most cases immediately available for further technical use.

The following Table shows the results of splitting ethylene to produce formaldehyde at different temperatures for the given composition of the gas mixture.

Table 1

| T (°C) | Conversion (%) | Selectivity (%) |
| --- | --- | --- |
| 340 | 2.41 | 92.8 |
| 375 | 5.26 | 90.1 |
| 400 | 7.9 | 85.0 |
| 440 | 15.8 | 84.4 |
| 465 | 26.3 | 80.8 |
| 490 | 32.8 | 78.6 |

EXAMPLE 2

Work was carried out as in Example 1 except that other mixture ratios of oxygen: ethylene were used. The results are summarized in the Table below.

Table 2

| % by vol. $O_2$ | % by vol. $C_2H_4$ | Conversion (%) | Selectivity (%) |
| --- | --- | --- | --- |
| 2.2 | 97.8 | 17.6 | 90.4 |
| 3.8 | 96.2 | 15.8 | 84.4 |
| 7.7 | 92.3 | 9.6 | 82.4 |

EXAMPLE 3

Work is carried out as in Example 1 except that nitrogen and/or carbon dioxide and/or water are added to the oxygen/ethylene mixture and the reaction carried out at 470°C in the presence of $Mo_9O_{26}$. Each gas composition and the resulting conversions and selectivities can be seen from the following Table.

Table 3

| Composition of the gas phase (% by vol.) | | | | | Conversion (%) | Selectivity (%) |
| --- | --- | --- | --- | --- | --- | --- |
| $O_2$ | $C_2H_4$ | $N_2$ | $CO_2$ | $H_2O$ | | |
| 5 | 5 | 90 | — | — | 14 | 77 |
| 5 | 5 | 73 | 17 | — | 14.5 | 76.2 |
| 5 | 5 | 87.2 | — | 2.8 | 13.8 | 77.6 |

EXAMPLE 4

Work was carried out as in Example 1 except that tungsten oxide of the formula $W_{20}O_{58}$ was used as the catalyst which was produced by reduction of $WO_3$ by 1.5 % $H_2O$-containing $H_2$ at 400° C. The reaction temperature was 340,° 405° and 480° C. The results are given in the following Table.

Table 4

| T (°C) | Conversion (%) | Selectivity (%) |
| --- | --- | --- |
| 340 | 6.45 | 83.4 |
| 405 | 24.1 | 80.3 |
| 480 | 39.5 | 77.6 |

EXAMPLE 5

0.7 l of ethylene and 25.9 l of air are conducted hourly at a reaction temperature of 570°C in the manner described in Example 1 over 10 g $WO_2$ as the catalyst present in a quartz boat and having a geometric surface of about 15 cm² (produced by reduction of $WO_3$ by 1.5 % water-containing hydrogen at 600°C). The conversion amounted to 17 % of the ethylene used. The formaldehyde yield was 62 % based on the conversion.

EXAMPLE 6

Work is carried out as in Example 1 except that carrier catalysts are used which are manufactured as follows:

a. Mo balls (diameter 3 – 6 mm) were oxidized at 720° C in air in a quartz boat over a period of 20 hours. Oxidation causes a thin oxide layer to appear on the metal as the carrier.

b. $SiO_2$ balls (diameter 1 – 3 mm), $SiO_2$ pellets length 5 – 8 mm) and $Al_2O_3$ pellets (length 5 – 8 mm) as the carrier are immersed in $(NH_4)_2MoO_4$, $(NH_4)_2WO_4$ or $(NH_4)VO_3$ solutions and the mixture evaporated. Thereafter the catalysts are heated at 600° C for several hours in an air stream.

The catalysts obtained according to (a) and (b) are treated as in Example 1 in 1.5 % $H_2O$-containing $H_2$. 8 cm³ of the finished catalysts are filled into the reaction tube. Thereafter, the ethylene/oxygen mixture described in Example 1 is conducted over the carrier catalysts at a temperature of 425°C. The results are shown in the Table below:

In order to give exact figures, the content of the catalytically active intermediary oxides was calculated as content of $MoO_3$, $WO_3$ and $V_2O_5$ respectively.

Table 5

| Catalyst | Conversion (%) | Selectivity (%) |
| --- | --- | --- |
| $MoO_3$ on Mo metal | 17.1 | 79.7 |
| molten $MoO_3$ | 11.5 | 80.4 |
| 7.3 % $MoO_3$ on $SiO_2$ | 13.4 | 67.3 |
| 1.4 % $MoO_3$ on $SiO_2$ | 18.8 | 78.6 |
| 0.15 % $MoO_3$ on $SiO_2$ | 14.4 | 68.5 |
| 6.2 % $WO_3$ on $SiO_2$ | 21.7 | 73.4 |
| 0.13 % $WO_3$ on $SiO_2$ | 16.8 | 71.0 |
| 7.3 % $MoO_3$ on $Al_2O_3$ | 13.1 | 63.6 |
| 1.3 % $WO_3$ on $Al_2O_3$ | 18.4 | 72.5 |
| 5 % $V_2O_5$ on $SiO_2$ | 28.8 | 23.0 | c. Work was carried out as in Example 6(b) except that the $SiO_2$ pellets were impregnated only with $(NH_4)_2MoO_4$ and after tempering at 600°C were introduced into the reaction tube. Under reaction conditions, after a short time, the catalyst turned blue and after about 20 minutes, the intermediary oxide had been formed. When using the catalyst thus obtained which had a content of intermediary oxide of, calculaed as $MoO_3$, 15 % by weight on $SiO_2$ pellets, the conversion was 23.2 based on the oxygen used, the selectivity being 79.6 %. These results of conversion and selectivity are practically the same during and after carrying out the experiment for a prolonged period of time, e.g. one week.

EXAMPLE 7

The splitting by oxidation of the double bond of propylene accompanied by the formation of acetaldehyde and formaldehyde was examined in the presence of molybdenum and tungsten oxide as catalysts, which were produced as in Examples 1 and 4. 1.06 l of propylene, 1.06 l of oxygen and 24.5 l of nitrogen were conducted hourly at 250° C over the catalysts. The conversions were 12 % based on the propylene used when using $W_{20}O_{58}$ as the catalyst and 16 % when using $Mo_9O_{26}$ as the catalyst. The ratio of the formaldehyde:acetaldehyde in the reaction product was 1.2 : 1. No acetone or acrolein could be detected.

EXAMPLE 8

Over the catalyst described in Example 1 there were conducted hourly at 370° C 25.6 l of isobutylene and 1 liter of oxygen at an overall-pressure of 1 atmosphere in the manner described therein. 12 % of the isobutylene were reacted. Acetone and formaldehyde were formed in a ratio of 1 : 1 at a selectivity of 36 %.

EXAMPLE 9

25 l of nitrogen were conducted hourly through an evaporation vessel in which α-methylstyrene was present, 2.8 g/h of α-methylstyrene being carried along in the nitrogen stream. 1.2 l of oxygen were added hourly to the gas stream thus obtained and the available starting gas conducted over $Mo_9O_{26}$ as the catalyst at 350° C in the manner described in Example 1. 18 % of the α-methylstyrene used were reacted. 62 % of the reacted α-methylstyrene were converted to acetophenone.

EXAMPLE 10

According to the method described in Example 9 a nitrogen stream of 25 l/h was loaded with 1.7 g/h of cyclopentene. The resulting gas mixture was mixed with 0.56 l/h of oxygen and conducted at 270° C over $W_{20}O_{58}$ as the catalyst. 14 % of the cyclopentene employed were reacted. 40 % of the reacted cyclopentene were oxidized to form glutardialdehyde.

Example 11

Over $Mo_9O_{26}$ as the catalyst, obtained according to Example 1, there were conducted at 340° C a mixture according to Example 9 consisting of 0.8 l/h cyclooctene, 1.3 l of oxygen/h and 24.5 l/h of nitrogen. The formation of octanedial as the reaction product was determined by infra-red and nuclear-resonance spectroscopic analysis.

It will be appreciated that the instand specification and examples are set forth by way of illustration and not limitation, and that various modifications and changes may be made without departing from the spirit and scope of the present invention.

What is claimed is:
1. In a process wherein an alkene hydrocarbon of the formula

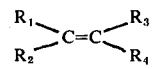

wherein
$R_1$, $R_2$, $R_3$ and $R_4$ each independently is hydrogen, an aryl group optionally substituted by at least one lower $C_1$–$C_4$ alkyl radical,
a straight-chain or branched alkyl radical with up to 18 C atoms, optionally phenyl substituted when lower alkyl, or
the radicals $R_1$ and $R_2$ together, or $R_3$ and $R_4$ together, contain not more than 20 C atoms and each, independently of each other, form a carbocyclic ring, or
the radicals $R_1$ and $R_3$ together with the C atoms of the C—C double bond are a carbocyclic ring with up to 24 C atoms and $R_2$ and $R_4$ each independently is hydrogen or a lower alkyl radical,
is oxidatively split with both C atoms of the double bond being converted to aldehyde or ketone functions, the improvement which comprises contacting the hydrocarbon for a time sufficient to produce said aldehyde or ketone functions with a gas consisting essentially of oxygen at about 150° to 650°C in the presence of a catalyst consisting essentially of at least one oxide of a metal selected from the group consisting of vanadium, niobium, tantalum, chromium, molybdenum, tungsten, uranium, manganese, technetium and rehenium, oxygen being present in about 0.02 to 50 times the molar amount of the alkene.

2. The process according to claim 1, wherein said oxide is an intermediary oxide.

3. The process according to claim 1, wherein the oxide has the formula $WO_{3-p}$ and $p$ is 0 or a positive number less than 3.

4. The process according to claim 1, wherein the oxide has the formula $MoO_{3-p}$ and $p$ is 0 or a positive number less than 3.

5. The process according to claim 1, wherein the oxide has the formula $VO_{2.5-x}$ and $x$ is 0 or a positive number less than 2.5.

6. The process according to claim 1, wherein the oxide has the formula $UO_{3-p}$ and $p$ is 0 or a positive number less than 3.

7. The process according to claim 1, wherein the oxide has the formula $ReO_{3.5-y}$ and $y$ is 0 nor a positive number less than 3.5.

8. The process according to claim 1, wherein the metal oxide is present on a carrier comprising silicic acid, natural or synthetic silicates, aluminum oxide, spinel, pumice stone or titanium dioxide, and the metal oxide is present in about 0.01 – 50% by weight of the metal oxide plus carrier.

9. The process according to claim 8, wherein the content of metal oxide in the catalyst is about 0.1 to 10% by weight, the reaction is carried out at a temperature of about 250° to 450°C, about 0.04 to 10 moles of oxygen are used per mole of unsaturated hydrocarbon, the oxygen being admixed with an inert gas selected from the group consisting of nitrogen, carbon dioxide and hydrogen, the inert gas comprising up to about 98% by volume of the gas mixture.

10. The process according to claim 1, wherein $R_1$, $R_2$ and $R_3$ each independently is hydrogen, a phenyl radical or a straight-chain or branched lower alkyl radical, and $R_4$ is hydrogen or a straight-chain or branched alkyl radical with up to 18 C atoms, one of the alkyl radicals $R^1$, $R^2$, $R^3$ and $R^4$ being substituted by a phenyl group optionally substituted by at least one lower alkyl radical.

11. The process according to claim 1, wherein the hydrocarbon has the formula

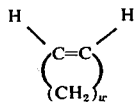

wherein $w$ is an integer from 3 to 22.

12. The process according to claim 1, wherein the hydrocarbon has the formula

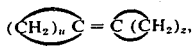

wherein $u$ and $z$ each independently is an integer from 4 to 11.

13. The process according to claim 1, wherein the hydrocarbon comprises ethylene.

14. The process according to claim 1, wherein the hydrocarbon comprises cyclopentene.

15. The process according to claim 4, wherein the hydrocarbon comprises ethylene.

* * * * *

UNITED STATES PATENT AND TRADEMARK OFFICE
CERTIFICATE OF CORRECTION

PATENT NO. : 3,946,081
DATED : March 23, 1976
INVENTOR(S) : Karl-Friedrich Wedemeyer et al.

It is certified that error appears in the above-identified patent and that said Letters Patent are hereby corrected as shown below:

Column 3, line 8, change "$\beta$-$WO_3$ to --$\alpha$-$WO_3$--;

line 26, change "sumation" to

--summation--.

Column 7, line 56, change "1-methyl-'-ethylidene-"

to -- 1-methyl-3-ethylidene- --.

Column 12, lines 67-68, change "calculaed" to

--calculated--.

Column 14, line 48, change "nor" to --or--.

Signed and Sealed this

Twenty-eighth Day of December 1976

[SEAL]

Attest:

RUTH C. MASON
*Attesting Officer*

C. MARSHALL DANN
*Commissioner of Patents and Trademarks*